United States Patent
Sanford et al.

(10) Patent No.: US 6,962,593 B2
(45) Date of Patent: Nov. 8, 2005

(54) TWO-PIECE CUT BLOCK FOR MINIMALLY INVASIVE SURGICAL PROCEDURE

(75) Inventors: Adam Sanford, Warsaw, IN (US);
Robert Hodorek, Warsaw, IN (US);
Roby Farling, Warsaw, IN (US)

(73) Assignee: Zimmer Technology, Inc., Chicago, IL (US)

( * ) Notice: Subject to any disclaimer, the term of this patent is extended or adjusted under 35 U.S.C. 154(b) by 0 days.

(21) Appl. No.: 10/161,946

(22) Filed: Jun. 4, 2002

(65) Prior Publication Data
US 2003/0225413 A1 Dec. 4, 2003

(51) Int. Cl.[7] .............................................. A61F 2/30
(52) U.S. Cl. ...................................................... 606/88
(58) Field of Search ........................... 606/87, 88, 89, 606/96; 623/13.12

(56) References Cited

U.S. PATENT DOCUMENTS

| | | | | |
|---|---|---|---|---|
| 5,462,549 A | * | 10/1995 | Glock | 606/86 |
| 5,741,264 A | * | 4/1998 | Cipolletti | 606/85 |
| 5,885,296 A | * | 3/1999 | Masini | 606/86 |
| 6,500,179 B1 | * | 12/2002 | Masini | 606/88 |

\* cited by examiner

*Primary Examiner*—Michael Milano
*Assistant Examiner*—D. Jacob Davis
(74) *Attorney, Agent, or Firm*—Jonathan D. Feuchtwang; Zimmer Technology, Inc.

(57) ABSTRACT

A two-piece cut block for performing a minimally invasive partial or total knee arthroplasty. The present invention comprises a cut block that can be inserted into an incision in two parts then assembled in vivo. The two-piece design allows the relatively large surgical instrument to fit into a small, minimally invasive, surgical incision

5 Claims, 4 Drawing Sheets

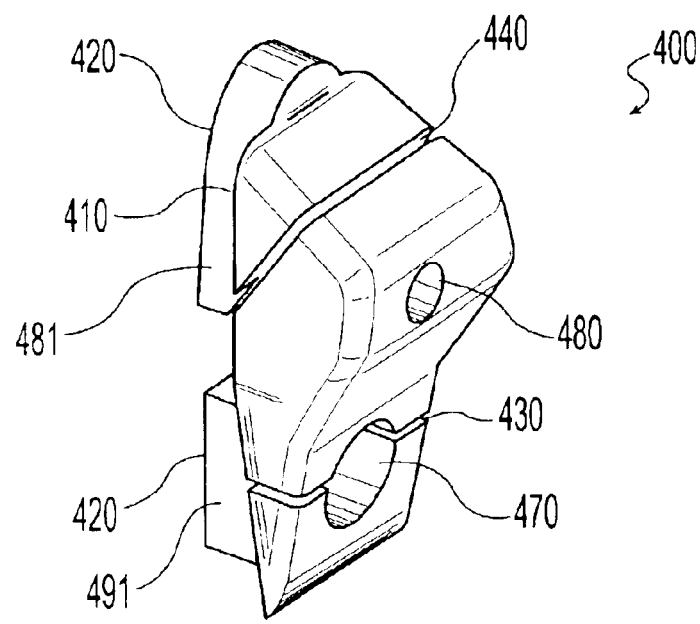
*Fig. 4*
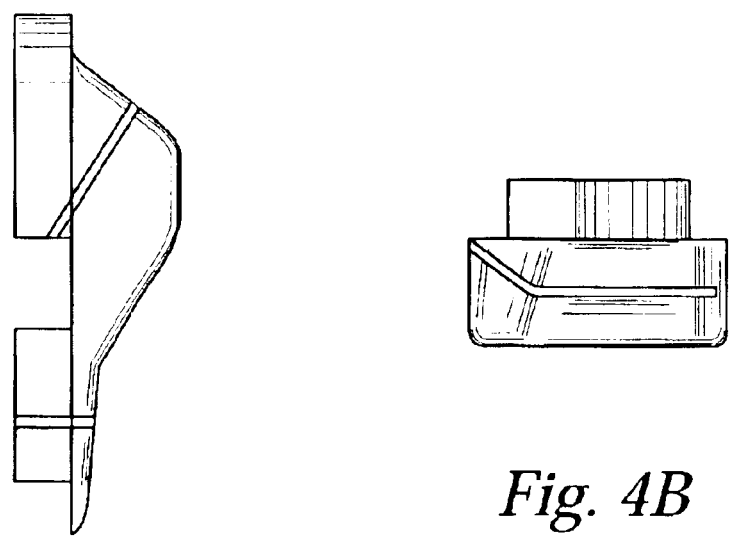
*Fig. 4B*
*Fig. 4A*

TWO-PIECE CUT BLOCK FOR MINIMALLY INVASIVE SURGICAL PROCEDURE

RELATED APPLICATIONS

There are no related applications.

BACKGROUND OF THE INVENTION

1. Field of the Invention

The present invention relates generally to medical instruments for aiding in the implantation of an endoprosthetic implant. More specifically, the present invention relates to a cutting guide for preparing a distal femur to accept the femoral component of a uni-condylar total knee implant during a minimally invasive surgical procedure.

2. Description of the Related Art

Partial knee replacement surgery has become relatively common. According to traditional practice, such surgeries require a relatively large incision through the soft tissue above a patient's knee, through which the various aspects of the partial knee arthroplasty are performed. These aspects include removing diseased bone and cartilage from the patient's knee and preparing the distal femur and proximal tibial to receive synthetic implants. For example, when a patient's knee deteriorates, cartilage wears away and the patient becomes either bow-legged or knock-kneed, depending on which side of the knee, medial or lateral, is diseased. Accordingly, surgery must be performed to realign the knee by seating artificial implants to replace the diseased portion of the patient's knee. Part of such a surgery involves resecting bone from the diseased side of the distal femur, such that the bone is appropriately shaped to receive an articulating artificial femoral component. In order to make sure such cuts are properly performed, and that soft tissue is not unnecessarily damaged, instruments called cut guides, which are well known in the art, are removably attached to the appropriate section of the distal femur, and are used to provide a mechanical stop to the saws introduced into the surgical field to make appropriate cuts on the distal femur. Larger surgical incisions naturally involve greater damage to skin, muscle connective tissue and the like, collectively referred to herein as soft tissues. As damage to a patient's soft tissue is increased, so too, is the time required for the patient to recover from surgery. This fact can cause a variety of negative economic effects. For example, a longer recovery time for a partial knee arthroplasty patient means a longer hospital stay. Physicians and hospitals, therefore, can accommodate fewer surgeries, and thus, the price to patients and their insurers increases for each individual surgery. Moreover, longer recovery times result in patients missing more time from work which may result in economic detriments for both the patient and his or her employer. However, a smaller incision results in a smaller scar and a generally more pleasing aesthetic effect for the patient.

Accordingly, minimally invasive surgical ("MIS") techniques have become available, which greatly reduce the size of the incision. Such smaller incisions, in the range of about 6–10 millimeters, vastly reduce the amount of time necessary for the patient to fully recover from a partial knee surgery. Thus, a need exists for minimally invasive surgical instruments that fit into smaller incisions, yet still useful to surgeons.

SUMMARY OF THE INVENTION

The present invention relates to a cutting guide for use in minimally invasive partial knee arthroplasty. In order to easily fit within the small incision of a minimally invasive surgical procedure, the cutting guide of the present invention comprises two pieces; a frame piece that removably attaches to a partially prepared distal femur; and a body piece that removably attaches to the frame piece. Both the frame piece and the body piece contain slots for accommodating surgical saws. These slots lie in mutual alignment when the body piece is removably attached to the frame piece. In use, the cutting guide of the present invention operates as a mechanical stop to saws and post drills used to perform the final preparations of the femur.

An advantage of the present invention is that by separating the cutting guide into two pieces, a surgeon can insert each piece into a surgical incision separately. Because the incision must accommodate only one component at a time, it can be smaller than if it had to accommodate both pieces at once. A smaller incision results in less initial trauma to the patient and therefore a faster recovery time.

Other advantages and features of the present invention will be apparent to those skilled in the art upon a review of the appended claims and drawings.

BRIEF DESCRIPTION OF THE DRAWINGS

FIG. 2A: perspective view of two piece cut block assembly attached to distal femor.

FIG. 4: perspective view of a cut block according to the present invention.

FIG. 4A: side elevation view of a cut block according to the present invention.

FIG. 4B: top view of a cut block according to the present invention.

DETAILED DESCRIPTION OF THE INVENTION

As used herein, the following locational definitions apply. Anterior and posterior mean nearer the front or nearer the back of the body respectively. Thus, for the knee joint described herein, anterior refers to that portion of the knee that is nearer the front of the body, when the leg is in an extended position. Proximal and distal mean nearer to or further from the root of the structure, respectively. For example, the distal femur is a part of the knee joint while the proximal femur is closer to the hip joint. Finally, the adjectives medial and lateral mean nearer the median plane or further from the median plane respectfully. The median plain is an imaginary vertical plane through the middle of the body that divides the body into right and left halves.

Figure 1:
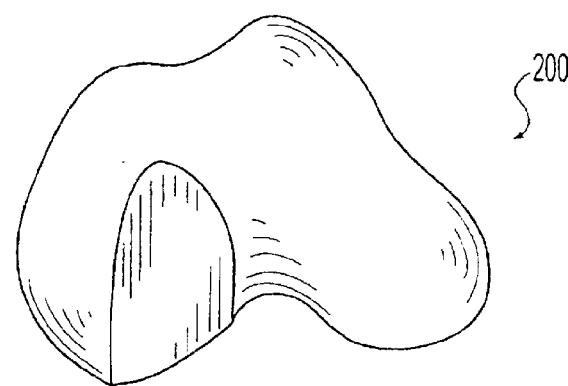
FIG. 1: perspective view of a partially prepared distal femur.
Figure 2:
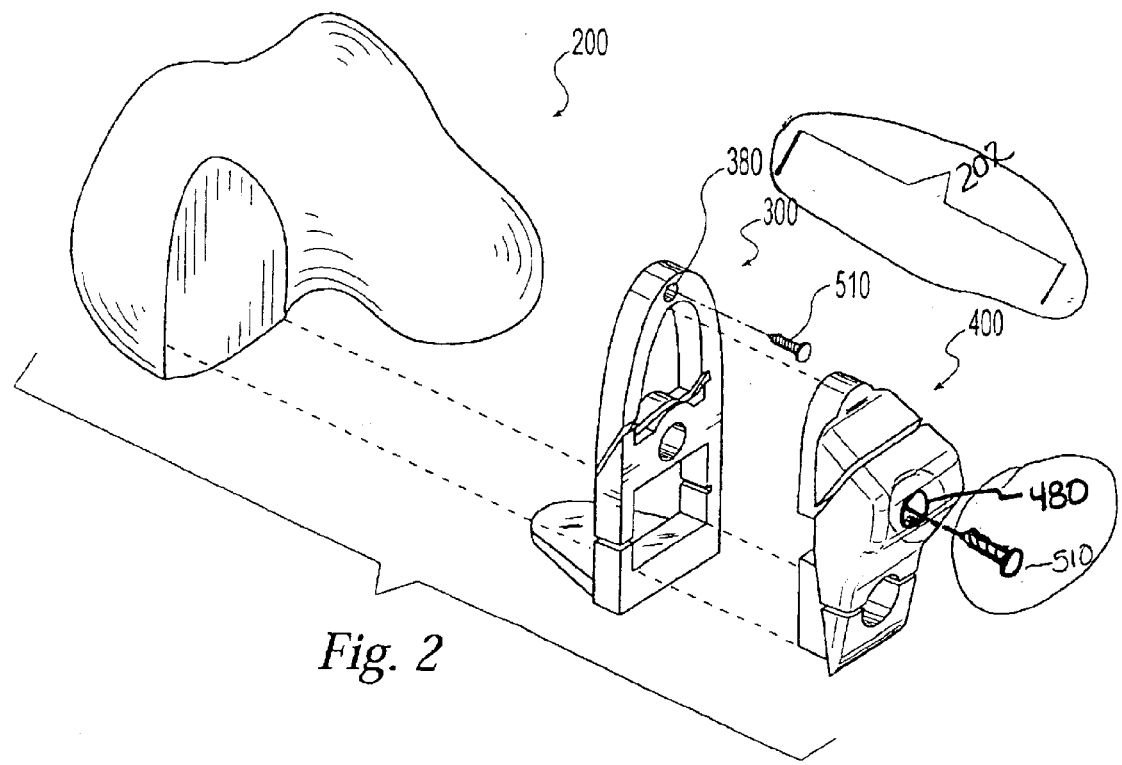
FIG. 2: exploded perspective view of the two-piece cut block assembly of the present invention.

Referring now to FIG. 1, there is shown a perspective view of a human knee showing the portion of the distal femur upon which the present invention can be used. FIG. 2 shows an exploded view of a two-piece cut block assembly 202 according to the present invention. FIG. 2 also shows a perspective view of partially prepared distal femur 200 (i.e. a distal femur having one condyle removed in preparation to receive a femoral condylar implant). For convenience, all of the descriptions and figures herein show the present invention used on only one side of the femur. It will be apparent to those skilled in the art, however, that a two-piece cut block according to the present invention can be used with either side of the femur yet remain within the scope of the present invention.

Figure 3:
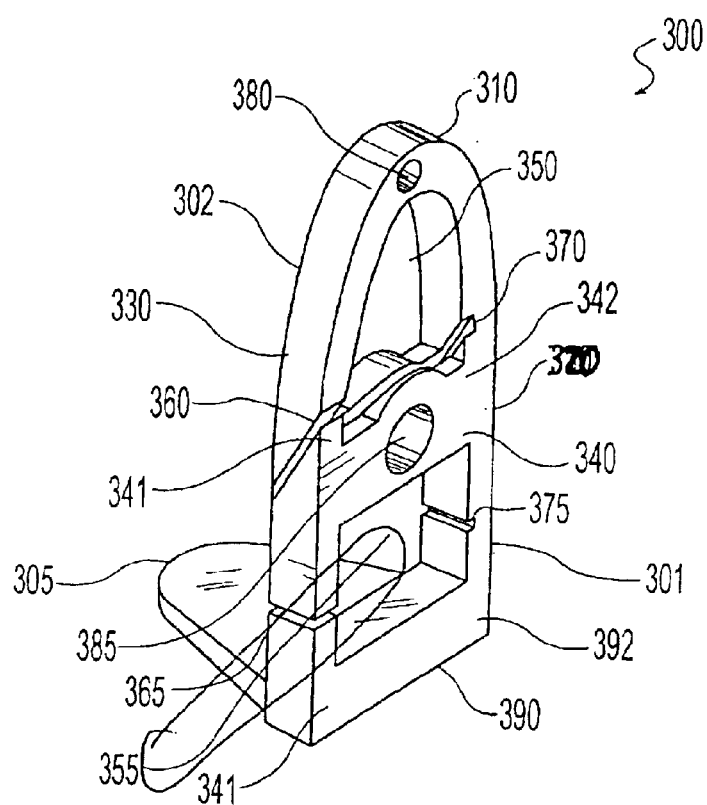
FIG. 3: perspective view of the frame according to the present invention.

Referring now to FIG. 2, there is shown an exploded prospective view of the two-piece cut block assembly 202 of the present invention, wherein assembly 202 comprises frame 300 and body 400. Turning now to FIG. 3, there is shown a perspective view of frame 300. Frame 300 comprises a generally arched anterior portion 310. Frame 300 further comprises lateral leg 320 and medial leg 330 that extend from arched portion 310 in a posterior direction. Disposed between legs 320 and 330 is cross member 340. Cross member 340 comprises opposing ends 341 and 342. End 342 of cross member 340 is fixedly attached to leg 330 such that leg 330 and cross member 340 are perpendicular. End 341 of cross member 340 is fixedly attached to leg 320 such that leg 300 and cross member 340 are perpendicular. Frame 300 further comprises anterior window 350. Window 350 is bound posteriorly by cross member 340, anteriorly by anterior portion 310, and by legs 320 and 330 on its lateral and medial sides, respectively. Anterior to cross member 340, are slot 360 and groove 370. Slot 360 is cut through leg 320 from the medial side of leg 320 through the lateral side of leg 320 at an angle corresponding to the angle of a desired cut to make on a particular femoral condyle. Groove 370 is cut into the lateral side of leg 330 at an angle equal to that of slot 360 such that a desired portion of the medial side of leg 330 remains intact as shown in FIG. 3. Slot 360 and groove 370 are co-planer and of sufficient size to accommodate a surgical bone cutting device. Slot 360 and groove 370 are of equal anterior/posterior height.

Figures 3A, 3B:
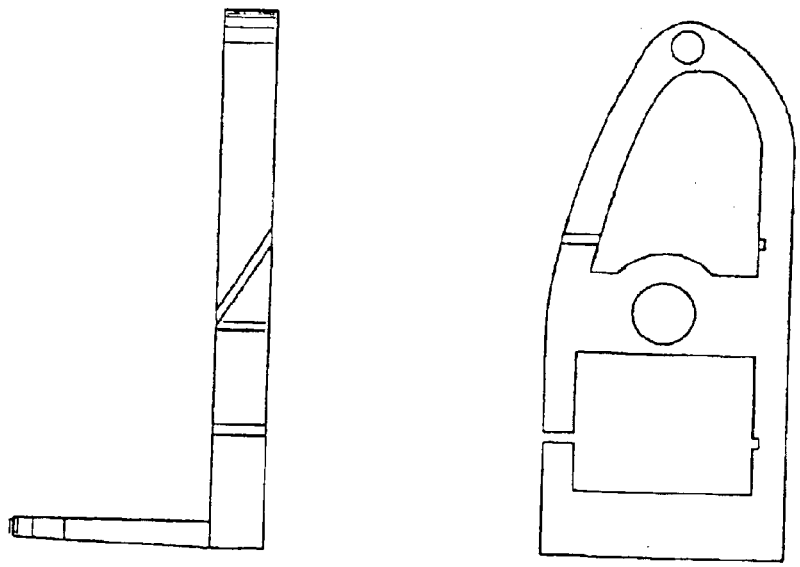
FIG. 3A: side elevation view of a frame according to the present invention.
FIG. 3B: front elevation view of a frame according to the present invention.

Frame 300 further comprises bone contacting surface 302 and free surface 301. Frame 300 further comprises bore 380 shown in FIGS. 3 and 3B. As shown in FIG. 3, bore 380 is located near the apex of portion 310 of frame 300 such that bore 380 is in communication with free surface 301 and bone contacting surface 302. As further shown in FIG. 3, frame 300 comprises threaded bore 385 through cross member 340, bore 385 is also in communication between surfaces 301 and 302, and is used with an insertion/removal instrument.

Frame 300 further comprises posterior window 355. Referring again to FIG. 3, legs 320 and 330 extend posteriorly beyond cross member 340 to bottom 390. Bottom 390 is disposed generally parallel to cross member 340. Bottom 390 extends between legs 320 and 330. Bottom 390 comprises opposing ends 391 and 392. End 392 of bottom 390 is fixedly attached to leg 330 such that leg 330 and bottom 390 are perpendicular. Similarly, end 391 of bottom 390 is fixedly attached to leg 320 such that leg 330 and bottom 390 are perpendicular. Posterior window 355 is bounded anteriorly by cross member 340, posteriorly by bottom 390, laterally by leg 320 and medially by leg 330. Posterior to cross member 340 in frame 300 are slot 365 and groove 375. Slot 365 is cut through leg 320 in a medial/lateral direction at a desired angle in a position posterior to cross member 340. Groove 375 is cut posterior to cross member 340 through only a desired amount of the lateral side of leg 330 such that the medial side of leg 330 remains intact. Slot 365 and groove 375 are co-planar, and both slot 365 and groove 375 correspond to a desired angle for a second femoral condylar resection cut. Continuing to refer to FIG. 3, there is shown foot 305. Foot 305 is connected to bottom 390 and protrudes perpendicularly from bone contacting surface 302 of frame 300 in a direction opposing free surface 301 of frame 300.

Referring now to FIG. 4, there shown cut block 400. Block 400 comprises free surface 420 and frame contacting surface 410. Free surface 420 is curved in the anterior/posterior plane. Frame contacting surface 410 includes groove 430. Groove 430 comprises a preferably rectangular cross-sectional shape, and is shaped appropriately to receive cross member 340 of frame 300 when block 400 is disposed on frame 300 in such a way that frame contacting surface 410 of block 400 abuts free surface 301 of frame 300.

Block 400 further comprises grooves 430 and 440. Groove 440 is positioned anteriorly to groove 430 and is in communication between free surface 420, frame contacting surface 410 and the lateral side of block 400. Groove 430 is positioned at an angle through block 400 corresponding to a desired angle for cutting the lateral portion of a femoral condyle. Groove 440 is also in communication with surface 420, surface 410, and the lateral side of clock 400.

Referring still to FIG. 4, block 400 further comprises bores 470 and 480. Bore 470 traverses slot 430 in a medial lateral direction such that surfaces 410 and 420 are in communication through bore 470. Block 400 further comprises threaded bore 480, which bore 480 is in communication between surfaces 410 and 420 of block 400. Bore 480 is disposed in block 400 such that it is concentric and in communication with bore 385 of frame 300 as shown in FIG. 2. Preferably bore 480 and bore 385 comprise equal diameters. In addition, bore 470 of block 400 is disposed therethrough such that the assembly of frame 300 and bore 400 results in the longitude axis of bore 470 being collinear with the center of window 385. In addition, bore 470 is disposed through block 400 along groove 430, such that groove 430 lies along the diameter of bore 470.

Figure 5:
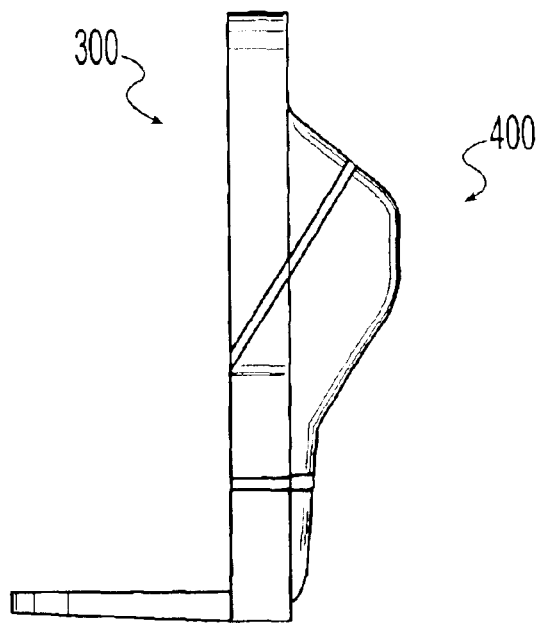
FIG. 5: side elevation view of a two piece cut block assembly according to the present invention, attached to a distal femur.
Figure 6:
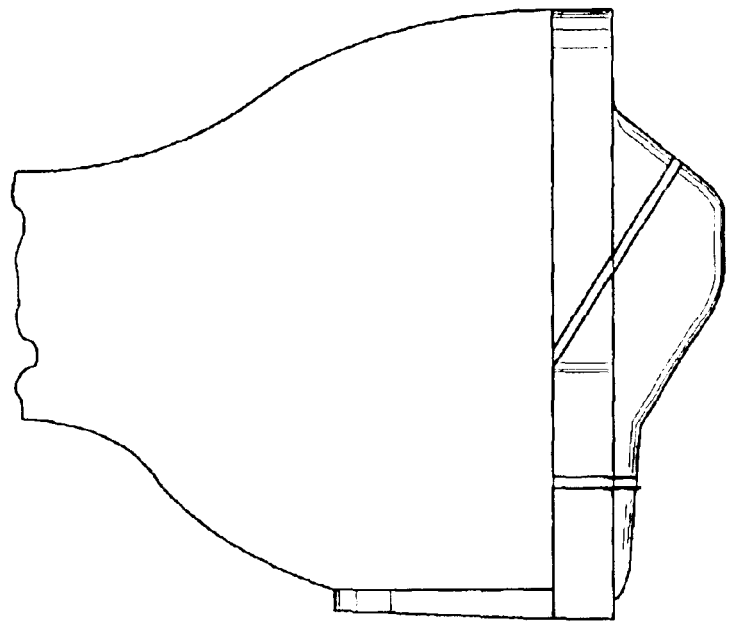
FIG. 6: side elevation view of a resected distal femur.

In FIG. 5, there is shown a side elevational view of an assembly according to the present invention. As shown in FIG. 5, surface 410 of block 400 is disposed against surface 301 of frame 300 such that block groove 400 is in co-planar with slot 360 and groove 370 while groove 430 is in co-planar with slot 365 and groove 375 of frame 300. In addition, slot 430 of block 400

During a partial knee replacement surgery, the two-piece cut block assembly is used as a cutting guide for surgical tools used to make the final cuts to distal femur 100 to prepare distal femur 100 to accept a femoral condylar implant. FIG. 5, shows assembled two piece cut block 202 attached to distal femur 200. A broad description of the surgery is as follows: After making an appropriate incision on the skin around the knee, the surgeon selects an appropriately sized frame 300 based on the size of the flat surface found on partially prepared distal femur 200. Frame 300 is inserted through an incision such that bone contacting surface 302 of frame 300 is adjacent to distal femur 200, and foot 305 is oriented toward the posterior side of distal femur 200. With a properly sized frame 300 in place, the surgeon drills a hole through bore 380 and into the distal femur 200. The surgeon then inserts a holding pin 510. At this point, distal femur 200 is still visible to the surgeon through frame windows 350 and 355. Next, the surgeon inserts body 400 through the incision (not shown) such that frame contacting surface 410 abuts free surface 301 of frame 300. Body 400 is disposed against frame 300 such that pads 481 and 491 are seated inside windows 350 and 355 respectively. Bore 480 is aligned with bore 385, such that seated, body 400 cannot rotate with respect to frame 300. Next, the surgeon drills a second hole, through bore 480 of body 400, and through bore 385 into distal femur 200. Another holding pin 510 is then inserted through this second series of holes to retain frame 300 and body 400 in place. Persons skilled in the art will appreciate that additional holes may be provided on either frame 300, body 400 or both, through which additional holes may be drilled into femur 200 and through which additional holding pins 510 may be placed. Finally, the surgeon drills a hole through body posterior pinhole 470 and window 355 into distal femur 200. At this point the surgeon leaves the drill in place.

Now that the two piece guide block assembly is in place, the surgeon can begin to make the final cuts to distal femur 200 in order to prepare distal femur 200 to accept a condylar implant. First, the surgeon removes the drill from bore 470 and window 355. Next, the surgeon inserts the blade of a surgical cutting device through cutting slots 440 and 360 and 370 and makes the appropriate cut to distal femur 200. Next, the surgeon removes holding pin 510 from bores 385 and 480. The surgeon then inserts the blade of a surgical cutting device through anterior cutting slots 450 and 365 and 375 and makes the appropriate cut to distal femur 200. Next, the final holding pin 510 is removed from frame 300. Thereafter, the surgeon removes body 400 from frame 300, and frame 300 from distal femur 200. Finally, the surgeon completes the remaining steps of the partial knee replacement, including installing a femoral condylar implant on a fully prepared distal femur 200.

It will be appreciated by those skilled in the art that the foregoing is a description of a preferred embodiment of the present invention and that variations in design and construction may be made to the preferred embodiment without departing from the scope of the invention as defined by the appended claims.

We claim:

1. An apparatus for guiding a resection device across a bone, the apparatus comprising a generally L-shaped frame, the frame comprising at least one slot and at least one groove co-planar with the slot and a relatively larger window facilitating an operator to see the bone there through and position the frame relative to landmarks on the bone, the slot and the groove adapted to guide a cutting portion of the resection device; a cut block, the cut block comprising at least one block groove adapted to guide the cutting portion of the resection device, and means for removably connecting the cut block to the frame such that at least one frame slot and at least one frame groove co-planar with at least one block groove.

2. The cutting guide apparatus of claim 1, wherein the means for removably attaching the cut block to the frame comprises a threaded aperture defined in the frame, a corresponding aperture defined in the cut block and at least one screw releasably securing attaching the cut block to the frame.

3. The cutting guide apparatus of claim 1, wherein the apparatus can be fit into an incision of about 1 cm to 6 cm in length.

4. The cutting guide apparatus of claim 1, wherein the apparatus can be fit into an incision of about 2 cm to 4 cm in length.

5. The cutting guide apparatus of claim 1, wherein the apparatus further comprises means for removably connecting the frame to the bone.

* * * * *

UNITED STATES PATENT AND TRADEMARK OFFICE
CERTIFICATE OF CORRECTION

PATENT NO. : 6,962,593 B2
DATED : November 8, 2005
INVENTOR(S) : Sanford et al.

It is certified that error appears in the above-identified patent and that said Letters Patent is hereby corrected as shown below:

Title page,
Item [75], Inventors, third inventor should read -- Toby Farling --.

Signed and Sealed this

Third Day of January, 2006

JON W. DUDAS
*Director of the United States Patent and Trademark Office*